United States Patent [19]
Perini et al.

[11] Patent Number: 5,703,690
[45] Date of Patent: Dec. 30, 1997

[54] OPTICAL GRANULOMETER FOR MEASURING THE CONCENTRATION OF PARTICULATE PRESENT IN A FLUID AT LOW STANDARD CONCENTRATIONS

[75] Inventors: Umberto Perini; Paolo Martinelli; Elena Golinelli; Sergio Musazzi; Franco Trespidi; Nice Pintus, all of Pisa, Italy

[73] Assignee: Enel S.p.A., Rome, Italy

[21] Appl. No.: 664,833

[22] Filed: Jun. 17, 1996

[30] Foreign Application Priority Data

Jun. 15, 1995 [IT] Italy .................. MI95A1286

[51] Int. Cl.⁶ .................................................. G01N 21/00
[52] U.S. Cl. ........................ 356/436; 356/441; 356/442
[58] Field of Search ............................ 356/436, 441–442; 359/507, 509, 511, 514

[56] References Cited

U.S. PATENT DOCUMENTS 4,999,514  3/1991  Silveston ............................ 356/343
5,303,036  4/1994  McLachlan et al. ................. 356/436

OTHER PUBLICATIONS

RM 41 Dust Density Monitor, SICK Optik Elektronik (excerpt from the approval issued by the Federal Ministry of the Interior (GMBI 1975, No. 36), (no month available).
Combustion Measurements, Edited by Norman Chigier, HOLVE et al., Chapter 8, "In Situ Particle Measurements in Combustion Environments", pp. 279–299, (no date available).
Auburn International Triboflow brochure, (no date available).

Primary Examiner—Frank G. Font
Assistant Examiner—Amanda Merlino
Attorney, Agent, or Firm—Keil & Weinkauf

[57] ABSTRACT

The granulometer uses a measuring laser beam (9) to illuminate particulate and, through the measure of the distribution of the light diffused by the examined particulate and gathered by a collecting lens (11), measures the concentration of particulate in the fluid in low concentration standards, the laser beam (9) being a converging one focused on a laser opaque shell (12) that partly covers the same lens.

4 Claims, 1 Drawing Sheet

U.S. Patent     Dec. 30, 1997     5,703,690
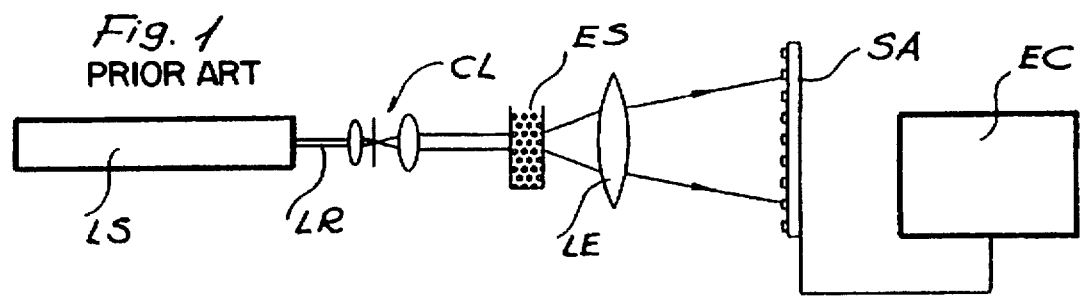
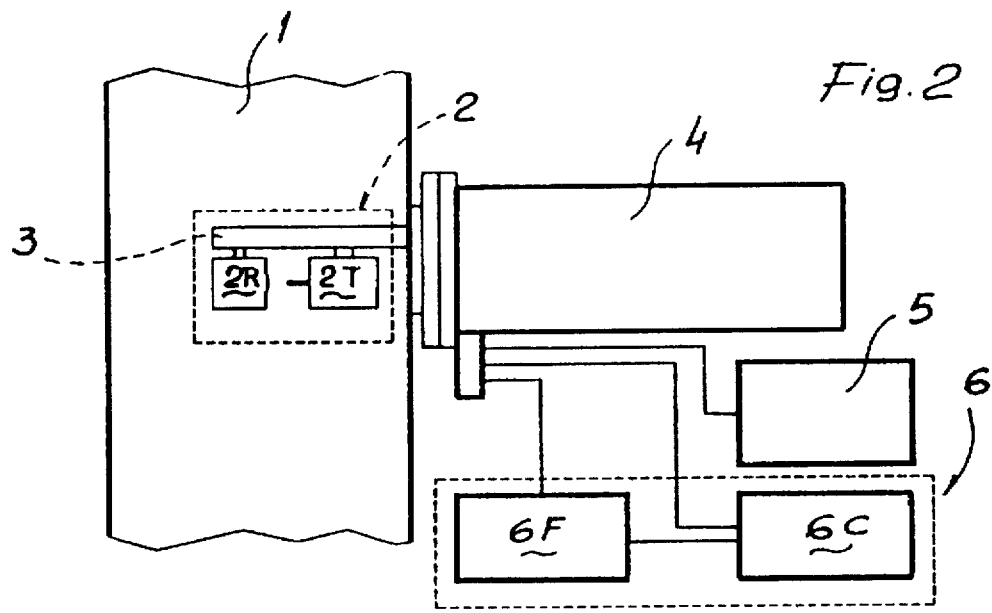
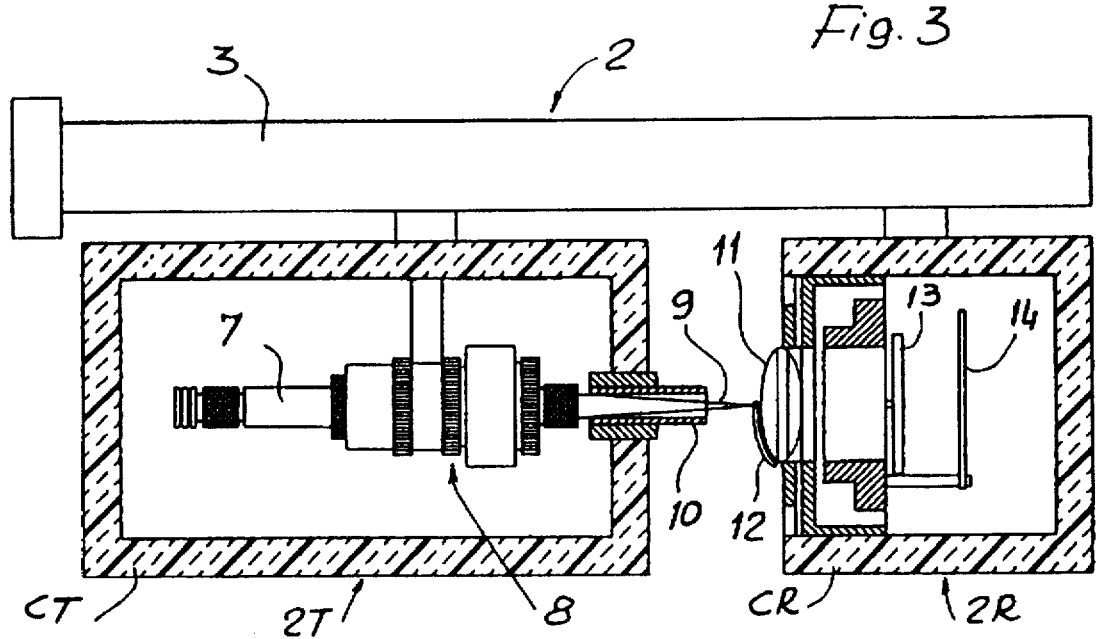

OPTICAL GRANULOMETER FOR MEASURING THE CONCENTRATION OF PARTICULATE PRESENT IN A FLUID AT LOW STANDARD CONCENTRATIONS

The present invention concerns an optical granulometer for measuring the concentration of particulate present in a fluid at low standard concentrations.

European regulations concerning the control of the emission of particulate materials by industrial plants rule for the in-line control of the concentration of particulates present in the gases emitted into the atmosphere by a plant. Such control is currently performed by means of measurements made using an opacimeter, sometimes combined with the measurement of the granulometric distribution performed in a laboratory by means of a granulometer on a sample of particulate gathered from the plant.

Opacimeters are optical instruments that measure the extinction of a light beam that propagates through the means examined. Because the extinction is that fraction of energy removed from the beam measured owing to diffusion and absorption phenomena, it is possible to relate back from the value of extinction to the measurement of particulate concentration provided the granulometric distribution of the particulate is known. The reliability of the measurement is obviously linked to the actual knowledge of the particulate's granulometry. Such granulometry is normally supposed to be constant through time and coinciding with that measured with the plant operating in nominal conditions. The drawbacks of this type of measurement are obvious: in the case of mat-functioning of the plant and hence with a possible alteration of the nominal granulometry of the particulate the resulting concentration values are affected by an error that is so much greater the greater are the differences in the real granulometric distribution compared to the normal granulometry of the particulate.

Another class of instruments is represented by granulometers that allow to determine the granulometric distribution and the concentration of the particulate. One should however state that granulometers are expensive instruments (more costly than opacimeters) and that there are not on the market granulometers suited to operating in-fine on an industrial plant in the experimental conditions set by this type of measurement.

The family of optical granulometers includes instruments based on the measurement of the light diffused by a particulate to determine its granulometric distribution. More especially, a sub-class of this family is represented by granulometers that are based on the measurement of the angular distribution of light diffused forwards at a low angle, as shown in FIG. 1. In these instruments the light diffused by the particulate (illuminated by means of a collimated laser beam) and gathered by an appropriate focusing lens. An array of detectors is set in the focal plane of the lens that allows the measurement of the light diffused at different angles. By means of appropriately developed algorithms it is possible to work back from the measurement of the angular distribution of the light intensity to the unknown granulometric distribution.

The contemporary measurement of the intensity of the beam transmitted, generally performed through a photodiode set co-axially to the analyzed beam in the focal plane of the lens, allows to determine the extinction of the same beam and hence, given that the granulometric distribution is known, to determine the concentration of the particulate. It is necessary, however, to make clear that this type of instruments is not suited to be used for in-line measurements on plants featuring low concentrations of particulate. The main reasons for these limits are:

1. The difficulty of performing measurements on highly diluted samples (in the current case of interest the concentration is about 100 times lower than that foreseen in normal operating conditions). In fact, in this case the signal/noise ratio of the signals measured becomes too low making a correct inversion of the diffusion data impossible;

2. Owing to the very low concentration (close to single particle standards) the cleanliness of the optical windows that confine the measurement volume becomes critical. In fact, if some particles of the fluid being examined should be permanently deposited on these surfaces, those particles would diffuse and absorb light in the same way as those in transit in the measurement region thus making both the estimate of the granulometric distribution and that of the concentration totally unreliable; for this reason the conventional optical granulometers cannot be used in-line on the plant where it would be extremely difficult to keep the optical windows that confine the transit zone of the particulate clean;

3. The instrument must operate at high temperatures and in the presence of corrosive substances. This involves mechanical stability problems (alignment), and of heat compatibility for both optical and electronic components and of wear to mechanical components.

The optical granulometer according to the present invention has the signal collecting lens partly covered, preferably for about half of its diameter, by a laser opaque shell, and preferably in the shape of a spherical part cap, that can allow the passage of a flow of air, previously filtered, that strikes the part of the lens that is not covered reducing the probability that a particle of particulate is deposited on the same lens.

Notwithstanding the presence of the above system for cleaning the collecting lens, it is practically impossible to keep the part of lens that is not covered completely clean. Because the presence of even very few particles on the lens corresponding to the laser beam transmitted would cause, at low concentration standards, large errors in the measurement of the concentration of particulate, it was necessary to find a different way of illuminating the particulate.

As will be better illustrated herein, the method found to illuminate the particulate consists in the use of a converging laser beam focused on said opaque shell, rather than a collimated laser beam that crosses the signal collecting lens.

The granulometer invented comprises three units:

a measuring head associated to a device to position the same head within the environment in which to perform the measurement, an electronic control unit, and a filtering and cooling system.

The measuring head consists of two units face to face and at a convenient distance (about 10 cm.): a first unit, conventionally called transmission unit, that contains a convenient laser source and an optical system to form the converging and focused measurement laser beam; a second unit, conventionally called receiving unit, that comprises the collecting lens, said opaque shell that partly covers the collecting lens and receives the focused laser beam, an array of sensors for the measurement of the light diffused and an electronic system to preamplify the signals. The particulate transits in the region comprised between the two units, is illuminated by the measurement laser beam and diffuses light in every direction. The array of photo-diodes, coaxial to the measurement beam and set in the focal plane of the collecting lens, gathers the light diffused forward and at a low angle.

The interface with the measurement fluid is different for the two above mentioned units:

- in the transmission unit the optical windows are absent because the laser beam passes through a tubelet through which a flow of air passes avoiding the entry of particulate into the same tubelet;
- the receiving unit receives laser light diffused by the particulate and borders with the flow of particulate by means of the collecting lens partly covered by said shell; the latter does not cause any shading of the light collected by the array of photo-diodes.

Said laser beam intercepted by said shell does not insist on the lens in such a way that the particulate present on it is not illuminated by the laser beam transmitted, but only of the light diffused and hence (apart from effects of the second kind) does not contribute to the luminous signal gathered by the array of sensors.

Illuminating with a converging focused laser beam generates a sliding of the diffusion figure in the detection plane; by appropriately dimensioning the optical focusing system it is however possible to obtain angular shifts of the diffusion lobe compatible with the geometry of the array of photo-detectors, in other words such as to not generate variations in the intensity measured higher than those acceptable to obtain a correct inversion of the diffusion data; as an alternative, it is possible to bear in mind this sliding effect by appropriately changing the inversion algorithm of the diffusion data.

The granulometer according to the present invention allows the measurement of the concentration of particles in a flow at low concentration standards by measuring the angular distribution of the intensity of the light diffused by the particulate, from which one can find the granulometric distribution of the same particulate and of the overall intensity of the light diffused in the solid angle projected by the array of photo-diodes; the two measurements combined allow to determine the concentration of the particulate.

Another feature of the granulometer invented is that the laser source (a laser diode) that originates said laser beam is piloted by a square wave signal, so that the intensity of the measuring laser beam periodically oscillates from zero to a maximum value and the detection of the signals exiting the array of photo-diodes takes place both in the period in which the laser beam is on and in the period in which the laser beam is off.

This feature of the granulometer invented offers the advantage of detecting noise, especially electronic noise, during the cycles in which the laser is off and subtract it from the signal measured during the cycles in which the laser is on, and this contributes to improving the signal/noise ratio also obtaining the performance of measurements with low concentrations of particulate.

Another advantage of the instrument invented is that the interception of the laser beam by the opaque shell leads to the elimination of possible errors due to the diffusion of light caused by the presence of particles on the surface of the lens and also this allows the instrument to operate also at very low concentrations.

The invention is illustrated in further detail below by means of an example of embodiment as illustrated in the attached drawings, where FIG. 1 shows a conventional granulometer based on the measurement of light diffused at a low angle, FIG. 2 is a general diagram, and FIG. 3 is the drawing of a measuring head of the granulometer according to the invention.

FIG. 1 shows a laser source LS from which the laser beam LR passes through a collimator CL, a sample of particulate being examined ES, a lens LE and strikes an array of sensors SA associated to an electronic control system EC.

FIG. 2 shows that inside a flue for fumes 1 a measuring head 2 is transversally positioned supported by an arm 3; the measuring head 2 comprises a transmission unit 2T and a receiving unit 2R:, external to the flue 1 is a container 4 in which the mechanism that enables the arm 3 to extend into the flue or retract from it is located; an electronic control system 5 and a filtering (6F) and cooling (6C) system are associated to the measuring head.

FIG. 3 shows the transmission 2T and receiving 2R units, each enclosed in a container CT, CR, of convenient insulating material; in the transmission unit 2T a laser source 7, an optical system 8 to form a laser beam 9 and the protection tubelet 10 for the laser beam exiting the unit are visible; in the receiving unit 2R lens 11 for collecting the diffused light, the metal shell 12 at a convenient distance from the lens in order to channel the air that deans the lens and intercept the laser beam 9, the array of photo-diodes 13 to analyze the light diffused and the board 14 of the electronic system foreseen to pre-amplify the signals exiting the array of sensors are visible. It is also well visible that the laser beam 9 is focused on the upper end of metal shell 12.

We claim:

1. An optical granulometer for measuring the concentration of particulate present in a fluid at low concentration standards, that uses a measuring laser beam to illuminate the particulate, by means of the measurement of the distribution of the light diffused by the particulate and gathered by a collecting lens with a focal length characterized in that the measuring laser beam is a converging laser beam focused on a laser opaque shell that partly covers said collecting lens.

2. An optical granulometer according to claim 1, said optical granulometer further comprising a measuring head, characterized in that the measuring head is made up of two units set face to face and at a distance in order to allow the passage in the space between one and the other of the particulate illuminated by the laser beam comprising a first unit containing a laser source that generates an amplitude modified laser beam and an optical system and comprises a second unit containing the collecting lens partly covered by said shell, an array of sensors to measure the light diffused and an electronic system to pre-amplify the signals, the array of sensors, coaxial to the laser beam and set in the focal plane of the collecting lens, gathers the light diffused forward and at a low angle.

3. An optical granulometer according to claim 1 characterized in that said opaque shell is set at a distance from said collecting lens so as to leave a space in which a flow of air is created that reduces the probability of particles being deposited on said collecting lens.

4. An optical granulometer according to claim 1, said optical granulometer further comprising a laser source and an array of sensors, characterized in that the laser source from which the laser beam originates is guided by a square wave signal that makes the intensity of the laser beam periodically oscillate from zero to a maximum value and causes the detection of signals exiting the array of sensors both in the period in which the laser is on and in the period when the laser is off.

* * * * *